United States Patent [19]

Schnorrenberg et al.

[11] Patent Number: 5,008,273
[45] Date of Patent: Apr. 16, 1991

[54] AMINO ACID DERIVATIVES AND THEIR PHARMACEUTICAL USE

[75] Inventors: Gerd Schnorrenberg, Gau-Algesheim; Otto Roos, Schwabenheim; Walter Lösel, Gau-Algesheim; Ingrid Wiedemann, Wiesbaden; Wolfram Gaida, Ingelheim/Rhein; Wolfgang Hoefke, Wiesbaden; Dietrich Arndts, Appenheim; Ilse Streller, Stromberg, all of Fed. Rep. of Germany

[73] Assignee: boehringer Ingelheim GmbH, Ingelheim am Rhein, Fed. Rep. of Germany

[21] Appl. No.: 403,628

[22] Filed: Sep. 6, 1989

Related U.S. Application Data

[60] Division of Ser. No. 284,164, Dec. 14, 1988, abandoned, which is a continuation of Ser. No. 127,750, Dec. 2, 1987, abandoned, which is a continuation of Ser. No. 897,444, Aug. 18, 1986, abandoned.

[30] Foreign Application Priority Data

Aug. 22, 1985 [DE] Fed. Rep. of Germany ....... 3529960

[51] Int. Cl.$^5$ ................... A61K 31/435; C07D 495/04
[52] U.S. Cl. ..................................... 514/301; 514/412; 546/87; 546/114; 546/118
[58] Field of Search ........................ 546/114; 548/453; 514/301, 412

[56] References Cited

U.S. PATENT DOCUMENTS 4,555,511 11/1985 Schnorrenberg et al. .......... 546/114

Primary Examiner—Bernard I. Dentz
Attorney, Agent, or Firm—David E. Frankhouser; Alan R. Stempel; Mary-Ellen M. Timbers

[57] ABSTRACT

Amino acid derivatives of general formula

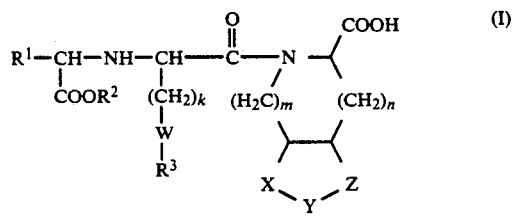

(the definitions of the various symbols being explained in the specification) are suitable for treating high blood pressure and for cardioprotection. The new compounds are prepared and used in the usual way.

14 Claims, No Drawings

AMINO ACID DERIVATIVES AND THEIR PHARMACEUTICAL USE

This is a division of application Ser. No. 284,164, filed Dec. 14, 1988, now abandoned, which in turn is a continuation of application Ser. No. 127,751 filed Dec. 2, 1987, now abandoned which in turn is a continuation of application Ser. No. 897,444, filed Aug. 18, 1986, now abandoned.

The invention relates to amino acid derivatives of general formula I and the salts thereof and processes for preparing them, pharmaceutical compositions containing them and their use as medicaments.

$$R^1-CH-NH-CH-\overset{O}{\overset{\|}{C}}-N\underset{(CH_2)_n}{\overset{COOH}{\diagdown}} \quad (I)$$
$$\underset{COOR^2}{|} \quad \underset{(CH_2)_k}{|} \quad (H_2C)_m$$
$$\underset{R^3}{\overset{W}{|}} \quad X\diagdown_Y\diagup Z$$

In this formula:
- $R^1$ represents hydrogen or an optionally phenyl-substituted alkyl group with 1 to 6 carbon atoms;
- $R^2$ represents hydrogen or an optionally phenyl-substituted alkyl group with 1 to 4 carbon atoms;
- $R^3$ represents hydrogen, an alkyl group with 1 to 7 carbon atoms which may have an amino group or a phenyl ring in the terminal position, or the group $R^4$—CO—;
- $R^4$ represents an alkyl group with 1 to 5 carbon atoms which, when W=NH, may have an amino group in the $\alpha$ position;
- W represents oxygen, sulphur or an NH group;
- n and m each represent 0, 1 or 2, the sum of n and m being 1 or 2;
- k represents 1, 2, 3 or 4;
- X, Y and Z represent oxygen, sulphur, $NR^5$, $CR^6$, $CHR^6$, $$\underset{-CH-CH-}{\overset{R^6 \quad R^6}{| \quad |}} \text{ or } \underset{C=C-}{\overset{R^6 \quad R^6}{| \quad |}},$$

with the proviso that only one of the X, Y and Z groups may represent O, S, $$\underset{-CH-CH-}{\overset{R^6 \quad R^6}{| \quad |}} \text{ or } \underset{C=C-}{\overset{R^6 \quad R^6}{| \quad |}},$$

and one or two of the groups X, Y and Z may represent $NR^5$;
- $R^5$ represents hydrogen or an alkyl group with 1 to 4 carbon atoms and
- $R^6$ represents hydrogen or, together with a vicinally situated group, $R^6$ represents a phenyl ring.

The 5- or 6-membered heterocyclic groups condensed onto the pyrrolidine- or piperidinecarboxylic acid may be saturated or unsaturated. Preferred heterocyclic groups include: furan, pyrrole, thiophene, benzofuran, indole, benzothiophene, oxazole, imidazole, thiazole, isoxazole, pyrazole, pyrrolidine, tetrahydrofuran, tetrahydrothiophene, pyridine, pyridazine, quinoline, isoquinoline or piperidine.

The new compounds generally have several centers of asymmetry and therefore occur as diastereomers or in the form of the racemates or racemic mixtures thereof. The invention includes both the racemic mixtures and also the individual diastereomers. Diastereomers wherein the central center of asymmetry and the center of asymmetry adjacent to $R_1$ occur in an S configuration are preferred. The center of asymmetry bonded to the nitrogen heterocycle may occur both in the R and also in the S configuration. By varying the stereochemistry at this center of asymmetry it is possible to influence the activity profiles towards a hypotensive activity and/or towards a cardioprotective activity.

The compounds of formula I may occur as zwitterions or, if free carboxyl groups are present, as alkali or alkaline earth metal salts, e.g. as sodium, potassium, magnesium or calcium salts and as the physiologically acceptable salts with amines such as trimethylamine or dicyclohexylamine. Furthermore, an existing free amino group may be reacted with an inorganic acid such as hydrochloric or hydrobromic acid or with an organic acid such as acetic acid to form a salt.

Preferred compounds of formula I correspond to the formula:

$$R^1-CH-NH-CH-CO-N\underset{(CH_2)_n}{\overset{COOH}{\diagdown}} \quad (Ia)$$
$$\underset{COOR_2}{|} \quad \underset{(CH_2)_4}{|} \quad (CH_2)_m \quad B$$
$$\underset{R^3}{\overset{NH}{|}} \quad \diagdown_A\diagup$$

wherein
$R^2$ and $R^3$ are defined as hereinbefore,
m represents 1 or 2,
n represents 0 or 1, the sum of m+n being equal to 2,
A represents one of the groups $$\diagdown_S \quad , \quad \underset{(A_2)}{\overset{|}{N}}\diagdown\underset{}{\overset{|}{N-R^5}} \text{ or }$$
(A₁)

$$\text{(benzene ring)}-\overset{|}{N}-R^5$$

(A₃)

wherein the groups $A_1$, $A_2$ and $A_3$ may be linked to the ring B in either way, and
$R^5$ is defined as hereinbefore.

Particularly notable are the compounds of formula $$\underset{\underset{\underset{NH-R^{3'}}{|}}{\overset{|}{(CH_2)_4}}}{\overset{COOR^{2'}}{C_6H_5-CH_2CH_2-CH-NH-CH-CO-N}} \overset{B}{\underset{(CH_2)_m}{\diagdown}} \overset{COOH}{\underset{(CH_2)_n}{\diagup}} \quad (Ib)$$

A' wherein $R^{2'}$ represents H or $C_{1-4}$ alkyl and $R^{3'}$ represents H or $COR^4$, wherein $R^4$ is as hereinbefore defined, m represents 1 or 2, n represents 0 or 1, the sum of m+n equaling 2, and A' represents one of the groups (A₁)    (A₂')    N—H or (A₃')

wherein the groups A₁, A₂, and A₃, may be linked to the ring B in either way.

Particular mention should be made of the following compounds:

N-[N-(1(S)-Ethoxycarbonyl-3-phenylpropyl)-L-lysyl]-4,5, 6,7-tetrahydro-thieno[3,2-c]pyridine-4(S)-carboxylic acid N-[N-(1(S)-Ethoxycarbonyl-3-phenylpropyl)-L-lysyl]-4,5, 6,7-tetrahydro-thieno[2,3-c]pyridine-7(S)-carboxylic acid N-[N-(1(S)-Carboxy-3-phenylpropyl)-L-lysyl]-4,5,6,7-tet rahydro-thieno[2,3-c]pyridine- 5(S)-carboxylic acid N-[N-(1(S)-Carboxy-3-phenylpropyl)-L-lysyl]-4,5,6,7-tet rahydro-thieno[3,2-c]pyridine-6(S)-carboxylic acid N-[N-(1(S)-Carbethoxy-3-phenylpropyl)-L-lysyl]-4,5,6,7-tetrahydro-thieno[3,2-c]pyridine-5(S)-carboxylic acid N-[N-(1(S)-Ethoxycarbonyl-3-phenylpropyl)-2-L-lysyl]-4, 5,6,7-tetrahydro-thieno[2,3-c]pyridine-5(S)-carboxylic acid N-[N-(1(S)-Carbethoxy-3-phenylpropyl)-L-lysyl]-4,5,6,7-tetrahydro-thieno[3,2-c]pyridine-6(S)-carboxylic acid.

The new substances of general formula I may be obtained by various methods:

(a) By reacting a compound of general formula $$\underset{\underset{\underset{R^8}{|}}{\overset{|}{(CH_2)_k}}}{\overset{O}{\overset{\parallel}{T-CH-C-N}}} \overset{COOR^7}{\underset{\underset{X\diagdown Y\diagup Z}{}}{\diagdown(CH_2)_n}} \quad (II)$$

with a compound of general formula III $$\underset{COOR^2}{\overset{R^1-CH-U}{|}} \quad (III)$$

wherein

T represents a nucleophilically displaceable group and

U represents an amino group or, conversely, T represents an amino group and U represents a nucleophilically displaceable group, $R^7$ represents hydrogen, an alkyl group with 1 to 4 carbon atoms, a benzyl group or a trimethylsilyl group, $R^8$ has the same meaning as $R^3$ or, if W represents—NH or W represents—S—and $R^3$ represents—H, $R^8$ may represent one of the protecting groups, tert.butyloxycarbonyl, benzyloxycarbonyl, fluorenylmethyloxycarbonyl, benzyl or trityl and the groups $R^1$, $R^2$, $R^3$, W, k, n, m, X, Y and Z are as hereinbefore defined.

Halides may be used as nucleophilically displaceable groups, so that 2-halocarboxylic acid derivatives and 2-amino acid derivatives may be used as starting materials, for example. The reaction is preferably carried out in polar solvents such as water, alcohols, dimethylformamide, acetonitrile, dimethylsulphoxide or mixtures thereof, optionally in the presence of alkali or alkaline earth metal carbonates, tertiary amines, quaternary ammonium hydroxides or tetraalkylguanidines. Depending on the solvent used, inversion of the halocarboxylic acid derivatives is observed and these should therefore preferably be used in the R configuration. After $R^7$ and/or $R^8$ have been split off by conventional methods, for example by acid or alkaline saponification of the ester or catalytic hydrogenolysis, the end products of general formula I are obtained.

(b) By reacting an α-oxocarboxylic acid derivative of general formula IV, $$\underset{COOR^2}{\overset{R^1-C=O}{|}} \quad (IV)$$

wherein $R^1$ and $R^2$ are as hereinbefore defined, with an amino acid amide of general formula II (T=NH₂) described in a), to obtain the corresponding imine which is then reduced. Suitable solvents for this reaction include water and alcohols and also non-polar solvents such as benzene or toluene. If anhydrous solvents are used, the water of reaction may be bound by adding molecular sieve. The reduction may be effected, for example, using sodium borohydride, sodium cyanoborohydride or by catalytic hydrogenation with palladium on charcoal or Raney nickel as catalysts.

In this reaction, when W=NH or W=S and $R^3$=H, the hydrogen atom must also be replaced by one of the protecting groups $R^8$.

The α-aminocarboxylic acid derivatives of general formula II (T=$NH_2$) are preferably used used in the S-configuration. In this case, depending on k, n, m, W, X, Y, Z, $R^7$ and $R^8$, asymmetrical induction is observed at the center of chirality which is still forming. If this induction is incomplete, the pure R or S form may be obtained by conventional methods of separation, preferably by fractional crystallisation and chromotographic separation of the diastereomers.

By splitting off $R^7$ and/or $R^8$ by conventional methods, as described by way of example, the end products of general formula I are obtained.

(c) Starting from a compound of general formula V

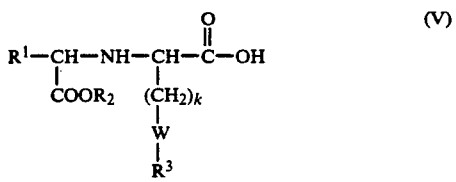

wherein $R^1$, $R^2$, $R^3$, W and k are hereinbefore defined, by reacting with an amino acid of formula VI

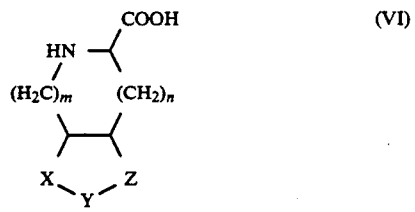

wherein the groups X, Y and Z and n and m are defined as hereinbefore, or by reacting with an ester of a compound of general formula VI ($R^7$ instead of hydrogen). In this reaction, if W=NH and W=S and $R^3$ H, the hydrogen atom must also be replaced by one of the protecting groups $R^8$.

Condensation may be effected using the methods described in Houben-Weyl, Methoden der Organischen Chemie, Volume 15. The preferred condensation agent for the reaction is N,N'-dicyclohexylcarbodiimide, the preferred carboxyl protecting group for the amino acid VI is the tert.butyl, methyl or trimethylsilyl group. After condensation, these and $R^8$ are split off by conventional methods as described above, for example.

The starting materials may be obtained by methods known per se.

The starting compounds II (T=halogen) are obtainable by condensing esters of amino acids of general formula VI with 2-halocarboxylic acids via the corresponding acid chlorides, mixed anhydrides, or active esters thereof or by other methods described in Houben-Weyl, Methoden der Organischen Chemie, Volume 15.

The compounds II (T=$NH_2$) are obtained by reacting esters of amino acids with N-protected aminocarboxylic acids. The amino protecting groups and condensation agents used are those described in Houben-Weyl, Methoden der Organischen Chemie, Volume 15. preferably, the t-butyloxycarbonyl or fluorenylmethoxycarbonyl group is used as the amino protecting group and N,N'-dicyclohexylcarbodiimide is used as condensation agent.

The starting compounds of general formula V are reacted to yield the corresponding imine, by reacting an α-oxocarboxylic acid derivative of general formula IV wherein $R^1$ and $R^2$ are as hereinbefore defined with an amino acid derivative of general formula VII

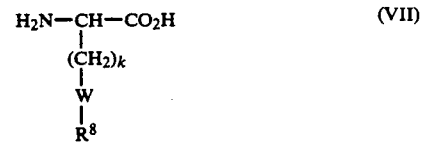

wherein k, W and $R^8$ are as hereinbefore defined, and are then reduced. Suitable solvents for this reaction include water, alcohols, alcohol/water mixtures and also non-polar solvents such as toluene. When anhydrous solvents are used the water of reaction may be bound by the addition of molecular sieve. The reaction may be carried out using sodium borohydride, sodium cyanoborohydride or catalytic hydrogenation with palladium on charcoal or Raney nickel as catalysts.

In this reaction, if W=NH or W=S and $R^3$=H, the hydrogen atom must be replaced by one of the protecting groups $R^8$.

The α-aminocarboxylic acid derivatives of general formula VII are preferably used in the S configuration. In this case, depending on the definitions of k, W and $R^8$, asymmetric induction is observed at the newly formed center of chirality. If this induction is incomplete, the pure R or S form may be obtained by conventional methods of separation, preferably by fractional crystallisation and chromatographic separation of the diastereomers.

By splitting off $R^8$ by conventional methods as described above, the end products of general formula I are obtained.

Starting compounds of general formula VI may be obtained, depending on the definitions of the groups X, Y and Z, by reacting (a) tryptamine and glyoxylic acid (B. T. Ho et al, J. pharm. Sci. 57, 269–274 (1968))

(b) thiophen-2-ethylamine and glyoxylic acid (J. P. Moffrand, Heterocycles 16, 35–37 (1981))

(c) tryptophan and formaldehyde (D. G. Harvey et al, J. Chem. Soc. 1941, 153–159)

(d) histidine and formaldehyde (M. Cain et al, Heterocycles 19, 1003–1007 (1982))

(e) from R- or S-β-2-thienylalanine and formaldehyde analogously to the reference mentioned in (c).

In the processes described above, the starting compounds may be present in the form of their racemic mixtures, diastereomers or enantiomers. If the racemic mixtures are used, the sterically uniform forms may be concentrated from the reaction products or obtained in pure form by conventional methods such as fractional crystallisation or chromatography.

Using the processes described hereinbefore, the following compounds may be obtained, for example:

N-[N-(1(S)-Ethoxycarbonyl-3-phenylpropyl)-L-lysyl]-4,5, 6,7-tetrahydro-thieno[3,2-c]pyridine-4(S)-carboxylic acid N-[N-(1(S)-Carboxy-3-phenylpropyl)-L-lysyl]-4,5.6,7-tetrahydro-thieno[3,2-c]pyridine-4(S)-carboxylic acid N-[N-(1(S)-Ethoxycarbonyl-3-phenylpropyl)-L-lysyl]-4,5,6,7-tetrahydro-thieno[2,3-c]pyridine-7(S)-carboxylic acid N-[N-(1(S)-Carboxy-3-phenylpropyl)-L-lysyl]4,5,6,7-tetrahydro-thieno[2,3-c]pyridine-7(S)-carboxylic acid N-[N-(1(S)-Carboxy-3-phenylpropyl)-L-lysyl]-2,3,4,9-tetrahydro-1H-pyrido[3,4-b]indole-3(S)-carboxylic acid N-[N-(1(S)-Carboxy-3-phenylpropyl)-L-lysy)]-4,5,6,7-tetrahydro-1H-imidazo[4,5-c]pyridine-6(S)-carboxylic acid N-[N-(1(S)-Carboxy-3-phenylpropyl)-L-lysyl]-4,5,6,7-tetrahydro-thieno[2,3-c]pyridine-5(S)-carboxylic acid N-[N-(1(S)-Carboxy-3-phenylpropyl)-L-lysyl]-4,5,6,7-tetrahydro-thieno[3,2-c]pyridine-6(S)-carboxylic acid N-[N-(1(R,S)-Carboxy-3-phenylpropyl)-L-seryl]-4,5,6,7-tetrahydro-thieno[2,3-c]pyridine-7(R,S)-carboxylic acid N-[N-(1(R,S)-Carboxy-3-phenylpropyl)-L-S-benzylcystein yl]4,5,6,7-tetrahydro-thieno[3,2-c]pyridine-4(R,S)-carboxylic acid N-[N-(1(R,S)-Ethoxycarbonyl-3-phenylpropyl)-L-o-acetylseryl]-4,5,6,7-tetrahydro-thieno[3,2-c]pyridine-4(R,S)-carboxylic acid N-[N$^\alpha$-(1(S)-Carboxy-3-phenylpropyl)-L-(N$^\epsilon$-glycy 1)-lysyl]-4,5,6,7-tetrahydro-thieno[3,2-c]pyridine-4(R,S)-carboxylic acid N-[N-(1(R,S)-Carboxy-3-phenylpropyl)-L-diaminopropionyl]-4,5,6,7-tetrahydro-thieno[2,3-c]pyridine-5(R,S)-carboxylic acid N[N$^\alpha$-(1(S)-Carboxy-3-phenylpropyl)-L-(N$^\epsilon$-tert.butyloxycarbonyl)-lysyl]-4,5,6,7-tetrahydro-thieno-[3,2-c]pyridine-6(S)-carboxylic acid N[N$^\alpha$-(1(S)-Carboxy-3-phenylpropyl)-L-(N$^\epsilon$-tert.butyloxycarbonyglycyl)-lysyl]-4,5,6,7-tetrahydro-thieno[3,2-c]pyridine-6(R,S)-carboxylic acid N[N$^\alpha$-(1(R,S)-Carboxy-3-phenylpropyl)-L-(N$^\epsilon$-propionyl)-lysyl]-4,5,6,7-tetrahydro-thieno[3,2-c]-pyridine-6(R,S)-carboxylic acid N-[N-(1(S)-Carboxy-3-phenylpropyl)-L-lysyl]-4,5,6,7-tet rahydro-thieno[3,2-c]pyridine-6(R)-carboxylic acid The new end products of general formula I have a powerful and long-lasting hypotensive activity. This is based on inhibition of the angiotensin I converting enzyme and hence on blocking the formation of the vasoconstrictor angiotensin II from angiotensin 1. In addition, the new compounds have an inhibitory effect on the enzyme kininase II which is responsible for the degradation of bradykinin, and which is regarded as identical to the converting enzyme mentioned above. Since bradykinin has a vasodilating effect, the hypotensive effect is intensified by this additional activity. The lowering in blood pressure produced by bradykinin in normal rats is intensified by the new compounds.

On the basis of their spectrum of activity, the compounds according to the invention are also suitable for the prevention of infarction and for reducing the myocardial oxygen requirements.

The following values were obtained for the inhibition of the isolated angiotensin converting enzyme:

| Compound according to Example | IC$_{50}$ [M] |
|---|---|
| 2 | 3.5 × 10$^{-9}$ |
| 4 | 1.8 × 10$^{-8}$ |
| 7 | 1.4 × 10$^{-8}$ |
| 10 | 2.9 × 10$^{-9}$ |

For lowering blood pressure the compounds may be administered by the intravenous, subcutaneous or oral routes. The dosage for oral administration is from 2-200 mg per dosage unit. For intravenous administration or when administered simultaneously with diuretics, it is advisable to reduce the dosage.

Furthermore, the new substances have a significant cardioprotectivity which was measured as follows:

As is well known, the myocardial Ca$^{++}$ level is a measure of hypoxic heart damage or heart damage caused by toxic doses of catecholamine (Higgins et al., MOL. CELL. CARDIOL. 10: 427–438, 1984; NAKANISHI et al., AM. J. PHYSIOL. 242: 437–449, 1982; FLECKENSTEIN A., Vortrage der Erlanger Physiol.

Tagung 1970, Edit. KEIDEL, Springer Verl. Berlin, Heidelberg, New York, 1971). Conversely, the inhibition of hypoxic or isoprenalin-induced myocardial calcium uptake is a measure of the cardioprotective efficacy of calcium antagonists (FLECKENSTEIN loc. cit.), of calmodulin inhibitors (HIGGINS) and other drugs, e.g. beta-adrenolytics (ARNDTS, ARZNEI-MITTEL FORSCH. 25: 1279–1284, 1975).

The cardioprotective activity was determined in conscious rats after subcutaneous or oral administration of the active substance using the method described by ARNDTS (loc.cit.) and the potency of the test substances was given as the H$_{50}$ value; this value corresponds to the dose which results in a 50% inhibition of the myocardial radio-calcium uptake caused by administration of 30 mg/kg s.c. of isoprenalin. The new compounds tested were found to be far more effective than the known commercial product nifedipin.

For a cardioprotective activity, the compound may be administered by the intravenous, subcutaneous or oral routes. The dosage for oral administration is from 2-200 mg per dosage unit.

For use in therapy, the new compounds are mixed with conventional pharmaceutical fillers or carriers, extenders, disintegrants, binders, lubricants, thickeners or diluents.

Examples of pharmaceutical preparations include tablets, capsules, suppositories, solutions, syrups, emulsions and dispersible powders, wherein if desired other known active substances such as saluretics, diuretics and/or antihypertensive agents may be added.

Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release such as carboxypolymethylene, carboxymethylcellulose, cellulose acetate phthalate or polyvinyl acetate. The tablets may also consist of several layers.

Coated tablets may be produced accordingly by coating cores made in the same way as the tablets with the substances normally used for tablet coating, such as collidone or shellac, gum arabic, talc, titanium dioxide or sugar. In order to obtain delayed release or prevent incompatibilities, the core may also consist of several layers. Similarly, the tablet coating may consist of several layers in order to obtain delayed release, and the excipients mentioned above for the tablets may be used.

Syrups of the active substances or combinations of active substances according to the invention may additionally contain a sweetener such as saccharine, cyclamate, glycerol or sugar and a flavour-enhancing agent, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Injection solutions are prepared in the usual way, e.g. by adding preservatives such as p-hydroxybenzoates or stabilizers such as alkali metal salts of ethylenediamine tetraacetic acid and by adding suitable solubilizing agents and the resulting solutions are transferred into injection vials or ampoules.

Capsules containing one or more active substances or combinations of active substances may be prepared, for example, by mixing the active substances with inert carriers such as lactose or sorbitol and encapsulating the mixture in gelatine capsules.

The following Examples serve to illustrate the invention:

EXAMPLE 1

N-[N-(1(S)-Ethoxycarbonyl-3-phenylpropyl)-L-lysyl]-4,5,6,7-tetrahydro-thieno[3,2-c]pyridine-4(S)-carboxylic acid (a)

N-(1-Ethoxycarbonyl-3-phenylpropyl)-L-N$^\epsilon$-t-butyloxycarbonyl-lysine

During 3½ hours, 37.7 g of NaCNBH$_3$ in 300 ml of ethanol are added dropwise to a solution of 247.5 g of ethyl 2-oxo-4-phenyl-butyrate and 74.2 g of N-t-butyloxycarbonyl-L-lysine in 1800 ml of 50% ethanol and the solution is then stirred for 12 hours at ambient temperature. Ethanol is evaporated off in vacuo and the aqueous phase is adjusted to pH 9 with 1 N sodium hydroxide solution and extracted three times with ether. The aqueous phase is then adjusted to pH 4 with 1 N HCl and extracted three times with ethyl acetate. The combined ethyl acetate extracts are dried over MgSO$_4$ and concentrated by evaporation in vacuo. 116 g of light yellow oil are obtained (88% of theory).

(b) t-Butyl N-[N-(1(S)-Ethoxycarbonyl-3-phenylpropyl)-L-N$^\epsilon$-t-butyloxycarbonyl-lysyl]-4,5,6,7-tetrahydrothieno[3,2-c]pyridine-4(S)-carboxylate 3.5 g of dicyclohexylcarbodiimide are added to a solution, cooled to 0° C., of 4.3 g of N-(1-ethoxycarbonyl-3-phenylpropyl)-L-N$^\epsilon$-t-butyloxycarbonyl-lysine, 3.3 g of t-butyl 4,5,6,7-tetrahydro-thieno-[3,2-c]pyridine-4-carboxylate, 2.1 g of 1-hydroxybenzotriazole and 2 ml of triethylamine in 40 ml of tetrahydrofuran and the mixture is then stirred for one hour at 0° C. and for 12 hours at ambient temperature. After filtration, the solution is concentrated by evaporation in vacuo, the residue is taken up in ethyl acetate, washed successively with 10$^{-3}$ N HCl, KHCO$_3$ solution and water, dried over MgSO$_4$ and evaporated down. The oil is chromatographed on silica gel (eluant: ethyl acetate/N-hexane (1:1)). The fractions with an R$_F$ value of 0.5–0.65 are purified together by HPLC chromatography (Polygosil 60-2540 of Messrs. Machery-Nagel) with ethyl acetate/n-hexane (1:1). The fractions with an R$^F$ value of 0.56 contain 1.8 g of t-butyl N-[N-(1(S)-ethoxycarbonyl-3-phenylpropyl)-L N-t-butyloxycarbonyl-lysyl]-4,5,6,7-tetrahydro-thieno[3,2-c]]pyridine-4(S)-carboxylate.

(c)

N-[N-(1(S)-Ethoxycarbonyl-3-phenylpropyl)-L-lysyl]-4,5,6,7-tetrahydro-thieno[3,2-c]pyridine-4(S)-carboxylic acid 1.8 g of the compound obtained in (b) are stirred into 200 ml of 1 N HCl in glacia acetic acid for 30 minutes at ambient temperature. The glacial acetic acid is distilled off in vacuo, the residue is treated with isopropanol/ether and the crystalline precipitate is filtered off, washed and dried. 1.1 g (80% of theory) of the dihydrochloride of the title compound are obtained. Mp: 162° C. (decomposition).

EXAMPLE 2

N-[N-(1(S)-Carboxy-3-phenylpropyl)-L-lysyl]4,5,6,7-tetrahydro-thieno[3,2-c]pyridine-4(S)-carboxylic acid (a)

Methyl N-[N-(1(S)-ethoxycarbonyl-3-phenylpropyl)-L-N$^\epsilon$-t-butyloxycarbonyl-lysyl]-4,5,6,7-tetrahydro-thieno[3,2-c]pyridine-4(S)-carboxylate 4.5 g of dicyclohexylcarbodiimide are added to a solution, cooled to 0° C., of 8.7 g of N-(1-ethoxycarbonyl-3-phenylpropyl)-L-N$^\epsilon$-t-butyloxycarbonyl-lysine, 4.6 g of methyl 4,5,6,7-tetrahydro-thieno- [3,2-c]pyridine-4-carboxylate hydrochloride, 3.06 g of 1-hydroxybenzotriazole and 5.6 ml of triethylamine in 75 ml of dimethylformamide/tetra- hydrofuran (1:1) and the resulting mixture is stirred for one hour at 0° C. and for 12 hours at ambient temperature. After filtration, the solution is concentrated by evaporation in vacuo, the residue is taken up in ethyl acetate, washed successively with 10$^{-3}$N HCl, KHCO$_3$ solution and water, dried over MgSO$_4$ and evaporated down. The oil is chromatographed over silica gel (eluant: ethyl acetate/n-hexane (1:1)). Fractions with an R$_F$ value of 0.4 are purified together by HPLC chromatography (Polygosil 60–2540 of Messrs. Machery-Nagel) using ethyl acetate/n-hexane (1:1). The fractions with an R$_F$ value of 0.38 contain 2.3 g of methyl N-[N-(1(S)-ethoxycarbonyl-3-phenylpropyl) L-N$^\epsilon$-t-butyloxycarbonyl-lysyl]-4,5,6,7-tetrahydro-thieno3,2-c]pyridine-4(S)carboxylate.

(b)

N-[N-(1(S)-Carboxy-3-phenylpropyl)-L-lysyl]-4,5,6,7-tetrahydro-thieno[3,2-c]pyridine-4(S)-carboxylic acid 2.3 g of the compound obtained in (a) are stirred with 12 ml of 1 N sodium hydroxide solution in 20 ml of acetonitrile for 12 hours at ambient temperature. The acetonitrile is distilled off in vacuo, the aqueous residue is extracted with ethyl acetate, neutralised with 1 N HCl and the precipitate is filtered off, washed and dried.

The crystals obtained are stirred with 20 ml of 1 N HCl in glacial acetic acid at ambient temperature for half an hour. The acetic acid is distilled off in vacuo, the residue is precipitated with isopropanol/ether, suction filtered and dried. 1.46 g (71% of theory) of the title compound are obtained in the form of a colourless amorphous powder.

Mp: 175–178° C. (decomp.).

EXAMPLE 3

N-[N-(1-(S)-Ethoxycarbonyl-3-phenylpropyl)-L-lysyl]-4, 5,6,7-tetrahydro-thieno[2,3-c]pyridine-7(S)-carboxylic acid As described in Example 1, 2.3 g of the title compound were obtained as the dihydrochloride from 8.6 g of N-(1-ethoxycarbonyl-3-phenylpropyl)-L-N$^\epsilon$-t-butyloxy- carbonyl-lysine and 6.6 g t-butyl 4,5,6,7-tetrahydro-thieno[2,3-c]pyridine-7-carboxylate.

EXAMPLE 4

N-[N-(1(S)-Carboxy-3-phenylpropyl)-L-lysyl]4,5,6,7-tetrahydro-thieno[2,3-c]pyridine-7(S)-carboxylic acid 0.9 of the title compound were obtained as the dihydrochloride as described in Example 2 from 4.4 g of N-(1-ethoxycarbonyl-3-phenylpropyl)-L-N$^\epsilon$-t-butyloxycarbonyl-lysine and 2.3 g of methyl 4,5,6,7-tetrahydro-thieno[2,3-c]pyridine-7-carboxylate hydrochloride.

Mp: 175° C. (decomp.).

EXAMPLE 5

N-[N-(1(S)-Carboxy-3-phenylpropyl)-L-lysyl]-2,3,4,9-tetrahydro-1H-pyrido[3,4-b]indole-3(S)-carboxylic acid From 4.4 g of N-(1-ethoxycarbonyl-3-phenylpropyl)-L-N$^\epsilon$ -t-butyloxycarbonyl-lysine and 2.7 g of methyl 2,3,4,9-tetrahydro-1H-pyrido[3,4-b]-indole-3(S)-carboxylate hydrochloride, 0.8 g of the title compound are obtained as the dihydrochloride, as described in Example 2.

Mp: 188° C. (decomp.).

EXAMPLE 6

N-[N-(1(S)-Carboxy-3-phenylpropyl)-L-lysyl]-4,5,6,7-tet rahydro-1H-imidazo[4,5-c]pyridine-6(S)-carboxylic acid From 4.4 g of N-(1-ethoxycarbonyl-3-phenylpropyl)-L-N$^\epsilon$-t-butyloxycarbonyl-lysine and 2.2 g of methyl 4,5,6,7-tetrahydro-1H-imidazo[4,5-c]pyridine-6(S)-carboxylate hydrochloride, 2.3 g of the title compound are obtained as the trihydrochloride, as described in Example 2.

Mp: 105° C. (decomp.).

EXAMPLE 7

N-[N-(1(S)-Carboxy-3-phenylpropyl)-L-lysyl]-4,5,6,7-tetrahydro-thieno[2,3-c]pyridine-5(S)-carboxylic acid From 11.2 g of N-(1-ethoxycarbonyl-3-phenylpropyl)-L-N$^\epsilon$t-butyloxycarbonyl-lysine and 6.0 g of methyl 4,5,6,7-tetrahydro-thieno[2,3-c]pyridine-5-carboxylate hydrochloride, 1.5 g of the title compound are obtained as the dihydrochloride as described in Example 2. Mp: 170° C. (decomp.).

EXAMPLE 8

N-[N-(1(S)-Carboxy-3-phenylpropyl)-L-lysyl]-4,5,6,7-tetrahydro-thieno[3,2-c]pyridine-6(S)-carboxylic acid From 5.5 g of N-(1-ethoxycarbonyl-3-phenylpropyl)-L-N$^\epsilon$ -t-butyloxycarbonyl-lysine and 3 g of methyl 4,5,6,7-tetrahydro-thieno[3,2-c]pyridine-6-carboxylate hydrochloride, 0.8 g of the title compound are obtained as the dihydrochloride as described in Example 2. Mp: 170° C. (decomp.).

EXAMPLE 9

N-[N-(1(S)-Ethoxycarbonyl-3-phenylpropyl)-L-lysyl]-4,5, 6,7-tetrahydro-thieno[2,3-c]pyridine-5(S)-carboxylic acid From 8.6 g of N-(1-ethoxycarbonyl-3-phenylpropyl)-L-N$^\epsilon$-t-butyloxycarbonyl-lysine and 6 6 g of t-butyl 4,5,6,7-tetrahydro-thieno[2,3 c]pyridine-5(S)-carboxylate, 2.0 g of the title compound are obtained as the dihydrochloride, as described in Example 1.

Mp: 106–109° C.

EXAMPLE 10

N-[N-(1(S)-Carboxy-3-phenylpropyl)-L-lysyl]-4,5,6,7-tetrahydro-thieno[3,2-c]pyridine-6(S)-carboxylic acid N-(1-(R,S)-Ethoxycarbonyl-3-phenylpropyl)-L-N$^\epsilon$-tert.butyloxycarbonyl-lysine obtained as in Example 1 (a) is taken up in ethyl acetate and mixed with anhydrous diethylether. The crystals precipitated overnight are filtered off and dried. About 60% of theory of N-(1(S)-ethoxycarbonyl-3-phenylpropyl-2(S)-N$^\epsilon$-tert.-butyloxycarbonyl-lysine are obtained in the form of colourless crystals.

4.4 g of this compound are reacted with 2.2 g of methyl 4,5,6,7-tetrahydro-thieno[3,2-c]pyridine-6(S)-carboxylate hydrochloride as described in Example 2. In a departure from this method, the product is purified over silica gel with ethyl acetate/n-hexane (1:1). 5.2 g (84% of theory) of methyl N-[N-(1(S)-ethoxycarbonyl-3-phenylpropyl-L-lysyl]-4,5,6,7-tetrahydro-thieno[3,2-c]pyridine-6 -(S)-carboxylate are obtained in the form of a colourless oil. This compound is reacted as described in Example 2 (b) to yield 3.0 g (75% of theory) of the title compound.

Mp: 170° C. (decomp.).

EXAMPLE 11

N-[N-(1(S)-Carboxy-3-phenylpropyl)-L-lysyl]-4,5,6,7-tetrahydro-thieno[3,2-c]pyridine-6(R)-carboxylic acid As described in Example 10, 1.4 g of the title compound are prepared in the form of colourless crystals from 2.2 g of N-(1(S)-ethoxycarbonyl-3-phenylpropyl)-L-N$^\epsilon$-tert.-butyloxycarbonyl-lysine and 1.1 g of methyl 4,5,6,7-tetrahydro-thieno[3,2-c]-pyridine-6(R)-carboxylate hydrochloride.

EXAMPLE 12

N[N-(1(S)-Carboxy-3-phenylpropyl)-L-N$^\epsilon$-tert.butyloarbonyl-lysyl]-4,5,6,7-tetrahydro-thieno[3,2-c]-pyridine-6(S)-carboxylic acid 7.8 g of methyl N-[N-(1(S)-ethoxycarbonyl-3-phenylpropyl)-L-N$^\epsilon$-tert.-butyloxycarbonyl-lysyl]-4,5,6,7-tetrahydrothieno[3,2-c]pyridine-6(S)-carboxylate obtained as described in Example 10 are stirred in 60 ml of acetonitrile/1 N sodium hydroxide solution (1:1)) for 12 hours at ambient temperature. The acetonitrile is distilled off, the aqueous residue is extracted with ethyl acetate, neutralised with 1 N HCl the crystals precipitated are filtered off, washed with diethylether and dried. 6.2 g of colourless crystals (90% of theory).

Mp: 123–125° C.

EXAMPLE 13

N[N$^\alpha$-(1(S)-Carboxy-3-phenylpropyl)-L-(N$^\epsilon$-tert.-butyloxycarbonylglycyl)-lysyl]-4,5,6,7-tetrahydrothieno[3,2-c]pyridine-6(R,S)-carboxylic acid (a) N$^\alpha$-Benzyloxycarbonyl-N$^\epsilon$-(tert.-butyloxycarbonylglycyl)-L-lysine 9 g of N$^\alpha$-benzyloxycarbonyl-L-lysine, 5.6 g of tert.-butyloxycarbonylglycine, 3.2 g of triethylamine, 4.9 g of 1-hydroxybenzotriazole and 7.9 g of N,N'-dicyclohexylcarbodiimide are stirred in 100 ml of THF/DMF (7:3) for 1 hour at 0° C. and over night at ambient temperature. After the urea has been filtered off the mixture is concentrated by evaporation, the residue is taken up in ethyl acetate, extracted with saturated KHSO$_4$ solution, washed with water, dried over MgSO$_4$ and concentrated by evaporation in vacuo. The residue is chromatographed over silica gel with methylene chloride/ethyl acetate/methanol (10:1:1). 12.5 g (100% of theory) are obtained in the form of a colourless oil.

(b) N-[N$^\alpha$-(1(S)-Ethoxycarbonyl-3-phenylpropyl)-N$^\epsilon$-(tert.-butyloxycarbonylglycyl)-L-lysine 12.5 g of the compound obtained in (a) are hydrogenated with 1.4 g of palladium-charcoal in 150 ml of methanol. After all the hydrogen has been taken up, the catalyst is filtered off and the filtrate is evaporated to dryness. The residue is stirred with 31.5 g of ethyl 2-oxo-4-phenylbutyrate and 4.7 g of sodium cyano- borohydride in 230 ml of ethanol/water (1:1) for 4 hours at ambient temperature. The ethanol is distilled off in vacuo, the aqueous solution is adjusted to pH 9, extracted with ethyl acetate and then adjusted to pH 3.5 with cold 1 N hydrochloric acid. It is extracted with ethyl acetate, the combined ethyl acetate phases are dried over MgSO$_4$ and concentrated by evaporation. The diastereomers are separated using an RP 18 column chromatograph with CH$_3$CN/water (80:20) as eluant and 4 g of the S,S-isomer are obtained and reacted to form the title compound as described in Example 2.

Mp.: 137° C.

EXAMPLE 14 (METHOD b)

(a) N$^\alpha$-benzyloxycarbonyl-N$^\epsilon$-t-butyloxycarbonyl-L-lysyl-L-spinacin methyl ester.

760 mg of N$^\alpha$-benzyloxycarbonyl-N$^\epsilon$-t-butyl-oxycarbonyl L-lysine, 436 mg of L-spinacin methyl ester hydrochloride, 456 mg of dicyclohexylcarbodiimide, 270 mg of 1-hydroxybenzotriazole and 200 mg of triethylamine are stirred in 15 ml of anhydrous dimethylformamide for 2 hours at ambient temperature. The mixture is washed twice each with KHSO$_4$ solution, NaHCO$_3$ solution and water, dried over MgSO$_4$ and concentrated by evaporation in vacuo. Colourless oil, 870 mg (80% of theory).

(b) N$^\epsilon$-t-Butyloxycarbonyl-L-lysyl-L-spinacin methyl ester 870 mg of the compound obtained in (a) are hydrogenated with 100 mg of palladium-charcoal in 20 ml of methanol. After all the hydrogen has been taken up the catalyst is filtered off and the filtrate is concentrated to dryness.

(c) N-[N-(1(R,S)-Ethoxycarbonyl-3-phenylpropyl)-N$^\epsilon$-t-butyloxycarbonyl-L-lysyl]-spinacin methyl ester A solution of 300 mg of sodium cyanoborohydride in 5 ml of ethanol is added dropwise to 650 mg of the compound obtained in (b) and 1.65 g of ethyl 2-oxo-4-phenylbutyrate in 10 ml of ethanol. The mixture is concentrated by evaporation in vacuo, the residue is taken up in ethyl acetate and washed with 10$^{-3}$N HCl and water. After drying over MgSO$_4$ the mixture is evaporated in vacuo and the oily residue is chromatographed on silica gel (eluant: ethyl acetate/n-hexane (1:1)). RF value=0.6. 770 mg of colourless oil are obtained.

(d) N-[N-1(R,S)-Carboxy-3-phenylpropyl)-L-lysyl]-L-spinacin

As described in Example 2, 620 mg of the title compound are obtained in the form of the trihydrochloride from 770 mg of the compound obtained in (c).

Mp.: 95° C.

EXAMPLE 15 (METHOD a)

N-[N-(1(R,S)-Ethoxycarbonyl-3-phenylpropyl)-N$^\epsilon$-t-butyloxycarbonyl-L-lysyl]-spinacin methylester 2.05 g of N$^\epsilon$-t-butyloxycarbonyl-L-lysyl-L-spinacin methylester are stirred overnight at ambient temperature in 50 ml of trifluoroethanol with 1.36 g of ethyl 2-bromo-4-phenylbutyrate and 530 mg of sodium carbonate. Trifluoroethanol is taken off in vacuo, the residue is taken up in ethyl acetate, washed with 10$^{-3}$N HCl and water, dried over MgSO$_4$ and concentrated by evaporation in vacuo. The oily residue is chromatographed over silica gel with ethyl acetate/n-hexane (1:1). Rf=0.6. 2.2 g are obtained in the form of a colourless oil.

Pharmaceutical Preparations (a) Coated tablets

| 1 tablet core contains: | |
| --- | --- |
| Active substance according to claim 1 | 20.0 mg |
| Lactose | 100.0 mg |
| Corn starch | 75.0 mg |
| Gelatine | 3.0 mg |
| Magnesium stearate | 2.0 mg |
| | 200.0 mg |

Method

The mixture of the active substance with lactose and corn starch is granulated with a 10% aqueous gelatine solution through a screen with a 1 mm mesh size, then dried at 40° C. and passed through a screen again. The granulate thus obtained is mixed with magnesium stearate and compressed. The resulting cores are coated in the usual way with a coating applied by means of an aqueous suspension of sugar, titanium dioxide, talc and gum arabic. The finished coated tablets are polished with bees-wax.

(b) Tablets

| | |
| --- | --- |
| Active substance according to claim 1 | 50.0 mg |
| Lactose | 100.0 mg |
| Corn starch | 70.0 mg |

-continued

| | |
|---|---|
| Soluble starch | 7.0 mg |
| Magnesium stearate | 3.0 mg |
| | 230.0 mg |

Method

The active substance and magnesium stearate are granulated with an aqueous solution of the soluble starch, the granulate is dried and intimately mixed with lactose and corn starch. The mixture is then compressed to form tablets weighing 230 mg, each containing 100 mg of active substance.

(c) Injection solutions

| | | |
|---|---|---|
| Active substance according to claim 1 | | 10.0 mg |
| Ethanolamine | | 60.0 mg |
| Sodium chloride | | 20.0 mg |
| Distilled water | ad. | 2 ml |

Method

The active substance and excipients are dissolved in sufficient distilled water and made up to the desired concentration with the necessary quantity of water. The solution is filtered and transferred into a 20 ml ampoules under aseptic conditions. The ampoules are sterilized and sealed. Each ampoule contains 50 mg of active substance.

(d) Capsules

| | |
|---|---|
| Active substance according to claim 1 | 20.0 mg |
| Lactose | 230.0 mg |
| Corn starch | 40.0 mg |
| Talc | 10.0 mg |
| | 300.0 mg |

Method

The active substance, lactose and corn starch are first mixed in a mixer and then in a grinding machine. The mixture is returned to the mixer, throughly mixed with the talc and mechanically packed into hard gelatine capsules.

(e) Suppositories

| | |
|---|---|
| Active substance according to claim 1 | 0.1 g |
| Cocoa butter (Fp. 36-37° C.) | 1.6 g |
| Carnauba wax | 0.1 g |
| | 1.8 g |

Method

The cocoa butter and carnauba wax are melted, thoroughly mixed and cooled to 45° C. The finely powdered active substance is stirred into this mess. The mixture is then poured into slightly chilled suppository moulds of suitable size and left to cool.

What is claimed is:

1. An amino acid derivative of the formula $$R^1-CH(COOR_2)-NH-CH((CH_2)_k-W-R^3)-CO-N\underset{(CH_2)_m\ (CH_2)_n}{\overset{B}{\diagup}}(COOH)\quad (I)$$

with ring A wherein

R$^1$ is hydrogen or an optionally phenyl-substituted alkyl group with 1 to 6 carbon atoms;

R$^2$ is hydrogen or an optionally phenyl-substituted alkyl group with 1 to 4 carbon atoms;

R$^3$ is hydrogen, an alkyl group with 1 to 7 carbon atoms which may have an amino group or a phenyl ring in the terminal position, or the group R$^4$—CO—;

R$^4$ is an alkyl group with 1 to 5 carbon atoms, which, when W=NH, may have an amino group in the α position;

W is oxygen, sulphur or an NH group;

n and m are each 0, 1, or 2, the sum of n and m being 1 or 2;

k is 1, 2, 3 or 4;

A is the group $$\underset{S}{\diagdown\diagup}$$

which may be linked to the ring B in either way; or a pharmaceutically acceptable salt thereof.

2. A compound as claimed in claim 1, having the formula $$R^1-CH(COOR_2)-NH-CH((CH_2)_4-NH-R^3)-CO-N\underset{(CH_2)_m\ (CH_2)_n}{\overset{B}{\diagup}}(COOH)\quad (Ia)$$

with ring A wherein m is 1 or 2, and n is 0 or 1, the sum of m+n being equal to 2.

3. A compound as claimed in claim 1, having the formula $$C_6H_5-CH_2CH_2-CH(COOR_{2'})-NH-CH((CH_2)_4-NH-R^{3'})-CO-N\underset{(CH_2)_m\ (CH_2)_n}{\overset{B}{\diagup}}(COOH)\quad (Ib)$$

with ring A' wherein

R$^2$' is H or C$_{1-4}$ alkyl and

R$^3$' is H or COR$^4$, wherein R4 is as hereinbefore defined, m is 1 or 2, and n is 0 or 1, the sum of m+n equaling 2.

4. A compound as claimed in claims 1, 2 or 3, characterized in that all the centers of asymmetry occur in the L-form.

5. In accordance with claim 1, N-[N-(1(S)-Ethoxycarbonyl-3-phenylpropyl)-L-lysyl]-4,5,6,7-tetrahydro-thieno]3,2-c]pyridine-4(S)-carboxylic acid, or a pharmaceutically acceptable salt thereof.

6. In accordance with claim 1, N-[N-(1(S)-Ethoxycarbonyl-3-phenylpropyl)-L-lysyl]-4,5,6,7-tetrahydro-thieno[2,3-c]]pyridine-7(S)-carboxylic acid, or a pharmaceutically acceptable salt thereof.

7. In accordance with claim 1, N-[N-(1S)-Carboxy-3-phenylpropyl)-L-Lysyl]-4,5,6,7-tetrahydro-thieno[2,3-c]pyridine-5(S)-carboxylic acid, or a pharmaceutically acceptable salt thereof.

8. In accordance with claim 1, N-[N-(1(S)-Carboxy-3-phenylpropyl)Llysyl]-4,5,6,7-tetrahydro-thieno[3,2-c]pyridine-6(S)-carboxylic acid, or a pharmaceutically acceptable salt thereof.

9. In accordance with claim 1, N-[N-(1(S)-ethoxycarbonyl-3-phenylpropyl)-L-lysyl]-4,5,6,7-tetrahydro-thieno[2,3-c]pyridine-5(S)-carboxylic acid, or a pharmaceutically acceptable salt thereof.

10. In accordance with claim 1, N-[N-(1(S)-ethoxycarbonyl-3-phenylpropyl)-L-lysyl]-4,5,6,7-tetrahydro-thieno[3,2-c]pyridine-6(S)-carboxylic acid, or a pharmaceutically acceptable salt thereof.

11. In accordance with claim 1, N-[N-(1(S)-Carboxy-3-phenylpropyl)-L-lysyl]-4,5,6,7-tetrahydro-thieno[3,2-]pyridine-6(R)-carboxylic acid, or a pharmaceutically acceptable salt thereof.

12. A pharmaceutical preparation containing a compound of formula I as claimed in claim 1, or a salt thereof, and a pharmaceutically acceptable carrier.

13. A pharmaceutical preparation containing a compound of formula I, as claimed in claim 1, or a salt thereof, in admixture with a saluretic, diuretic or antihypertensive agent.

14. A method for treating high blood pressure, the prevention of infarction or reducing the myocardial oxygen consumption which comprise administering an effective amount of a compound of formula I, as claimed in claim 1, or a pharmaceutically acceptable salt thereof.

* * * * *